United States Patent [19]

Finley

[11] 4,381,406
[45] Apr. 26, 1983

[54] PROCESS FOR MAKING ALLYLIC ESTERS OF TETRACHLOROPHTHALIC ACID

[75] Inventor: Joseph H. Finley, Metuchen, N.J.

[73] Assignee: FMC Corporation, Philadelphia, Pa.

[21] Appl. No.: 303,648

[22] Filed: Sep. 18, 1981

[51] Int. Cl.$^3$ ....................... C07C 67/00; C07C 67/08
[52] U.S. Cl. ........................................ 560/83; 560/96; 560/98
[58] Field of Search ............................. 560/83, 96, 98

[56] References Cited

U.S. PATENT DOCUMENTS

| | | | |
|---|---|---|---|
| 2,073,937 | 3/1937 | Kyrides | 560/83 X |
| 2,296,823 | 9/1942 | Pollack et al. | 560/201 |
| 2,462,601 | 2/1949 | Bohrer | 560/83 |
| 2,923,634 | 2/1960 | Lindemann | 560/83 X |
| 3,086,985 | 4/1963 | Stange et al. | 560/96 |
| 3,148,207 | 9/1964 | Weinkauff et al. | 560/96 |
| 3,250,801 | 5/1966 | Stange et al. | 560/96 |
| 3,336,366 | 8/1967 | Dill | 560/95 |
| 3,418,360 | 12/1968 | Schulz et al. | 560/96 |
| 3,465,030 | 9/1969 | Leumann et al. | 560/96 |
| 3,483,247 | 12/1969 | Mills et al. | 560/85 |
| 4,105,710 | 8/1978 | Thomas et al. | 260/869 |

FOREIGN PATENT DOCUMENTS 633876 12/1949 United Kingdom .

OTHER PUBLICATIONS

Guseinov, M. M., et al., "Production of Esters of Tetrachlorophthalic Anhydride," *Azerb. Khim. Zh.*, 6, 21–23 (1964).

Parish, R. C. et al., "A Method for the Esterification of Hindered Acids," *J. Org. Chem.*, 30, 927–929 (1965).

Matsumoto, A. et al., "Studies of the Polymerization of Diallyl Compounds, XX," *J. Poly. Sci., Polymer Chem. Ed.*, 11, 2365–2368 (1973).

Borsini, G. et al., "French Pat. No. 1,372,967," *Chem. Abstracts*, 62, 2742 (1965).

Nordlander, B. W. et al., "The Esterification of Tetrachlorophthalic Anhydride," *J. Amer. Chem. Soc.*, 69, 2679–2682 (1947).

*Primary Examiner*—Natalie Trousof
*Assistant Examiner*—Vera C. Clarke
*Attorney, Agent, or Firm*—Richard E. Elden; Eugene G. Horsky

[57] ABSTRACT

Allylic esters of tetrachlorophthalic acid are formed using allylic alcohol both as a reactant and a solvent. In the first step, the alcohol and a base are reacted with tetrachlorophthalic anhydride to form the half-ester sodium salt. In the second step, the sodium salt is reacted with allylic halide to form the diester which crystallizes from solution. The excess solvent may be treated to recover the raw materials or recycled.

17 Claims, No Drawings

PROCESS FOR MAKING ALLYLIC ESTERS OF TETRACHLOROPHTHALIC ACID

This invention relates to the production of diallylic esters of tetrachlorophthalic acid.

It has long been known that the addition of halogens imparts flame retardant properties to polymers. In addition, Matsumoto et al have found that diallyl tetrachlorophthalate (DATCP) and diallyl tetrabromophthalate (DATBP) readily could form copolymers with vinyl and vinylidine-unsaturated compounds, such as diallyl phthalate, allyl benzoate, and vinyl acetate (*Journal of Polymer Science: Polymer Chemistry Edition*, Part A-1, Volume 11 (1973), 2365–2368). Although diallyl phthalate has been prepared by direct acid catalyzed esterification of phthalic anhydride with exess allyl alcohol, DATCP, DATBP, and other diallylic esters are difficult to produce from tetrahalophthalic acid or anhydride because the tetrachlorophalate and tetrabromophthalate radicals are sterically hindered. Primarily, only the monoester of each is formed by direct esterification with allylic alcohol. Even when the water of reaction has been removed by distillation, only trivial yields of DATCP have been obtained. In addition, allyl alcohol is reactive and readily forms unwanted ethers, aldehydes, hydrocarbons, and polymers.

Using a method similar to the known preparation of diallyl phthalate by reacting allyl chloride with metal salts of phthalic acid, Matsumoto et al prepared DATCP by reacting disodium tetrachlorophthalate with 2 moles of allyl chloride in an aqueous solution containing cuprous ions. Diallyl tetrachlorophthalate was also produced by Guseinov et al who reacted the anhydride with 3 moles of allyl alcohol plus 1 mole of hydrochloric acid in a benzene solution (*Azerbaizhan Chemical Journal*, No. 6, (1964), 21–23). Nordlander et al also produced DATCP by reacting the tetrachlorophthalic anhydride with 2 moles of allyl alcohol using sulfuric acid as a catalyst and driving off the water of reaction by distillation as an azeotrope with benzene (*Journal of the American Chemical Society*, 69, Nov., (1947), 2679–2682). However, only a 10% to 15% yield of the DATCP was obtained because of dehydration and polymerization reactions of the allyl alcohol.

Diallyl phthalate also has been prepared using allyl chloride by a two-step process, described in U.S. Pat. No. 3,465,030. In the first step, phthalic anhydride is reacted with sufficient allyl alcohol to form only the monoester; in the second step, allyl chloride is reacted with the monoester in the presence of quaternary ammonium salt or a tertiary amine to form diallyl phthalate. This process requires the reaction of a solid and a liquid which can form a very thick, paste-like intermediate phase and is not feasible for a commercial process. The process of U.S. Pat. No. 3,465,030 confines the allyl alcohol to the first step, avoiding any alcohol in the second step.

According to the present invention, DATCP and similar allylic esters are prepared from tetrachlorophthalic anhydride in a two-step procedure using an allylic alcohol in sufficient quantities to serve not only as a reactant in the first step in which the allylic half-ester or a salt of the half-ester is formed, but also as a solvent for reactants and products in both steps. In the second step, an allylic halide is reacted with the monoester to produce the diester in the presence of the allylic alcohol surviving the first step.

At the reaction temperatures employed in the second step the diester is soluble in the allylic alcohol solvent, but the diester is not substantially soluble in the allylic alcohol at room temperature and thus the diester can be crystallized and recovered from the solution by cooling.

Allyl alcohol is a unique solvent for DATCP synthesis. DATCP is soluble in allyl alcohol at the reaction temperature which is above the melting point of DATCP (72.0° C.–73.5° C.). Upon cooling the allyl alcohol, DATCP crystallizes from the reaction mixture. Since most impurities remain dissolved in the allyl alcohol, DATCP can be purified by washing with small amounts of water to remove the allyl alcohol traces. No further purification step is needed.

The semi-esterification reaction of the first step may be carried out in the presence of a base which forms a salt with the monoester. Any suitable base can be used, even a strong base such as sodium hydroxide, which might be expected to hydrolyze the ester. Contrary to such expectation, it was found that it was not necessary to add the base after the monoester was formed but that it could be included in the reaction mixture at the start of the first step.

The word "base" is used herein in the broadest sense, that is, as an acceptor of protons, and the term includes any salt of a weak acid capable of forming a corresponding salt with the monoallylic tetrachlorophthalate ester. Thus, sodium or potassium carbonate can be used, as well as the corresponding hydroxides or organic bases, such as triethylamine. The preferred base is sodium carbonate. Ordinarily, the base will be present in an amount approximately equivalent to the monoester resulting in the conversion of substantially all the monoester to the salt; however, a small excess of the base can be present, up to for instance, about 10% over the equivalent amount.

An esterification catalyst will ordinarily be used in both the first and second steps in order to facilitate the reaction. Of the known esterifcation catalysts, tertiary amines may be used for the first step and tertiary amine halides may be used for the second step. Allylic triethylammonium chloride has been found especially suitable in the second step.

Any catalytic amount of these catalytic materials can be used. It is ordinarily suitable to use an amount of catalyst in the first step between about 1 mole percent and 10 mole percent of the amount of tetrachlorophthalic anhydride. When a tertiary amine is used as the base, it will also function as an esterification catalyst. In the second step, it is ordinarily suitable to use an amount of catalyst between 10 mole percent and 40 mole percent of the amount of the tetrachlorophthalic anhydride initially introduced into the process. When an allylic triethylammonium cloride is used as the catalyst in the second step, it can be added as such or formed in situ from triethylamine carried over from the first step, plus allylic chloride added in a sufficient amount over that required for the diester formation.

Although only a sufficient excess of allylic alcohol need be present as a solvent in the first and second steps to insure an adequate reaction rate, it is ordinarily desirable that the excess be sufficient to maintain substantially all reactants and reaction products in solution at the respective reaction temperatures. It is ordinarily desirable that at least about 5 moles, and preferably at least about 10 moles of allylic alcohol per mole of tetrachlorophthalic anhydride be provided in the first step. The upper limit of the amount of allylic alcohol is dictated only by economic considerations and the increased difficulty of recovering diester from the solution. Ordinarily, there is no advantage in using more than about 20 moles to 25 moles of allylic alcohol per mole of tetrachlorophthalic anhydride.

If desired, other solvents which do not adversely affect the reaction can be used in conjunction with the allylic alcohol solvent if the resultant solvent mixture is such that the diester is not substantially soluble in it at a room temperature so that the diester can be crystallized from the solution. For instance, a solvent mixture of allylic alcohol and diallylic ether can be used. Even when an additional solvent is provided it is desirable, however, that a minimum of about 5 moles of allylic alcohol per mole of tetrachlorophthalic anhydride be provided for the first step. There is, ordinarily, no advantage in providing more than about 20 moles to 25 moles of such solvent mixture per mole of tetrachlorophthalic anhydride.

The first and second steps of the process can be carried out in the same or different vessels. The rate at which the semi-esterification proceeds in the first step is dependent upon the temperature of the reactants. Starting at room temperature, with no external application of heat, the reaction will require many hours for completion. It is, therefore, desirable to heat the reaction mixture to accelerate the reaction. When the reaction mixture is heated to the preferred temperature range of about 90° C.–95° C., the reaction will ordinarily be completed in from about ½ hour to about 2 hours. This first step reaction can conveniently be carried out at atmospheric pressure, preferably under reflux.

The second step is preferably carried out at temperatures of from about 100° C. to about 110° C. Because of the boiling point of allylic halides, this reaction will ordinarily be carried out in a sealed autoclave in which pressure of from about 103 kPa to about 172 kPa (15 to 25 psig) will be generated at these temperatures. The reaction will ordinarily be completed in about 2 hours.

The water generated by the formation of the monoester in the first step does not appear to have an adverse effect on the second step and there is evidence that this small amount of water may, in fact, be beneficial. The mixture resulting from the first step may, therefore, be used directly in the second step, with the addition of the components required to complete the reaction mixture for the second step.

The diester produced in the second step can be recovered by cooling the solution to room temperature to cause crystallization of the diester, separating the diester from the remaining solution, and washing the residual solution from the diester with water. The solution from which the diester was separated can be recycled to the process, or the components of the solution can be recovered by a procedure similar to that described below.

In the preferred embodiment of this invention for the production of DATCP, 1 mole of tetrachlorophthalic anhydride, 0.55 mole of sodium carbonate (or 1 mole of sodium hydroxide), and a catalytic amount (0.024 mole) of triethylamine are added to a large excess (up to 10–20 moles) of allyl alcohol as a solvent as well as a reactant. If sodium hydroxide is used as the base, it is convenient to dissolve it in the allyl alcohol before the addition of the tetrachlorophthalic anhydride. The mixture is stirred and heated to 90° C.–95° C. to speed the reaction to completion, yielding a solution or a thin suspension of the sodium salt of monoallyl tetrachlorophthalate.

After the completion of this step, 1.2 moles of allyl chloride plus a catalytic amount (0.33 mole) of allyltriethylammonium chloride (either preformed or formed in situ from triethylamine and additional allyl chloride) are added and the mixture is heated in a closed vessel for 2 hours at 100° C.–110° C., developing an equilibrium pressure of 103 kPa–172 kPa (15–25 psig). Longer heating may be required if no pressure is allowed to develop. On cooling, the DATCP crystallizes and the separated product requires only washing with cold water and drying. The washing may be accomplished by merely spraying with water in a centrifuge.

After the DATCP is isolated the mother liquor may be recycled, or the raw materials may be recovered. For example, the recovery may be accomplished by first distilling off the low-boiling allyl chloride and allyl alcohol, then adding water plus an excess of a base, and distilling a trimethylamine-water azeotrope. The solution is next neutralized and tetrachlorophthalic acid is recovered by filtration. The acid is dried by distilling a water-toluene azeotrope from the wet acid.

The process of this invention is illustrated in the following non-limiting Example.

EXAMPLE I

A mixture of 28.6 g tetrachlorphthalic anhydride, 128.3 g allyl alcohol (5.8 g as a reactant and 122.5 g as a solvent), 0.73 g triethylamine as catalyst, and 5.3 g sodium carbonate was stirred and heated to 90° C.–95° C. for 45 minutes to give a hazy, pale-yellow solution. The solution was cooled to room temperature and transferred to a stainless steel, rocking-pressure reactor and 14.5 g allyl bromide was added together with 5.0 allytriethylammonium bromide as a catalyst. The reactor was sealed and heated to 100° C.–110° C. for two hours. A pressure of 103 kPa–172 kPa (15–25 psig) developed. The reactor was then cooled to room temperature and the contents removed. The solid present was filtered, washed with cold water, was then dried under vacuum at 40° C.–50° C. A 59% yield (17 g) of DATCP was recovered, with a melting point of 72.0° C.–73.5° C.

I claim:

1. The method of producing a diallylic ester of tetrachlorophthalic acid comprising the steps of:
   (a) forming a salt of the monoallylic ester of tetrachlorophthalic acid by reacting tetrachlorophthalic anhydride with
      (i) a sufficient excess of allylic alcohol, over the amount to form the said monoallylic ester, to comprise at least part of a solvent to maintain in solution or suspension the said salt formed in (a), and
      (ii) a sufficient amount of a base to form said salt,
   (b) adding to the product of step (a) a sufficient amount of an allylic halide to convert the salt of the monoallylic ester to the diester of tetrachlorophthalic acid and heating to accelerate the reaction,
   (c) cooling the solution produced in step (b) to crystallize the said allylic diester of tetrachlorophthalic acid from solution, and
   (d) separating the thus-created allylic diester of tetrachlorophthalic acid from the remaining solvent.

2. The method of claim 1 in which a catalytic amount of a tertiary amine is present in step (a).

3. The method of claim 2 in which the amine is triethylamine.

4. The method of claims 1, 2, or 3 in which a catalytic amount of a quaternary ammonium halide is present in step (b).

5. The method of claim 4 in which the quaternary ammonium halide is allyltriethylammonium chloride.

6. The method of claim 1 in which the allylic alcohol is allyl alcohol.

7. The method of claim 4 in which the allylic alcohol is allyl alcohol.

8. The method of claim 1 in which the allylic alcohol is present in step (a) in an amount of at least 5 moles per mole of tetrachlorophthalic anhydride.

9. The method of claim 1 in which the allylic alcohol is present in step (a) in an excess sufficient to retain in solution all reactants and reaction products in steps (a) and (b) at the reaction temperatures of those steps.

10. The method of claim 7 in which step (a) is carried out at a temperature of about 90° C.–95° C. and step (b) is carried out in a closed vessel at a temperature of about 100° C.–110° C.

11. The method of claim 1 in which the allylic alcohol is methallyl alcohol.

12. The method of claim 6 or 11 in which the allylic halide is allyl chloride.

13. The method of claims 6 or 11 in which the allylic halide is methallyl chloride.

14. The method of claim 1 in which the base is sodium carbonate.

15. The method of claim 1 in which the base is sodium hydroxide.

16. The method of claim 1 in which at least part of the solvent from step (d) is reused in step (a) (i).

17. The method of producing diallyl tetrachlorophthalate comprising the steps of:
  (a) forming the sodium salt of monoallyl tetrachlorophthalate by heating tetrachlorophthalic anhydride with allyl alcohol at a temperature of about 90°–95° C. in the presence of a sufficient amount of sodium carbonate to form the sodium salt of the monoallyl tetrachlorophthalate which is produced and in the presence of a catalytic amount of triethylamine, said allyl alcohol being present in an amount of at least 10 moles per mole of tetrachlorophthalic anhydride, the excess allyl alcohol acting as a solvent for the reactants,
  (b) adding to the product of step (a) sufficient allyl chloride to convert the sodium salt of monoallyl tetrachlorophthalate to diallyl tetrachlorophthalate and heating in a closed vessel to a temperature of about 100° C.–110° C. until the diallyl ester is formed, and
  (c) cooling the product of step (b) to crystallize the diallyl tetrachlorophthalate from solution in the excess allyl alcohol.

* * * * *